United States Patent [19]
Dijkgraaf et al.

[11] Patent Number: 5,837,292
[45] Date of Patent: Nov. 17, 1998

[54] GRANULATE FOR THE PREPARATION OF FAST-DISINTEGRATING AND FAST-DISSOLVING COMPOSITIONS CONTAINING A HIGH AMOUNT OF DRUG

[75] Inventors: Bernardus Leonardus Johannes Dijkgraaf, Delft; Aart Mühlenbruch, Haarlem, both of Netherlands

[73] Assignee: Yamanouchi Europe B.V., Netherlands

[21] Appl. No.: 770,421

[22] Filed: Dec. 20, 1996

[30] Foreign Application Priority Data

Jul. 3, 1996 [EP] European Pat. Off. .............. 96201829

[51] Int. Cl.$^6$ .................................. A61K 9/16; A61K 9/20
[52] U.S. Cl. ........................ 424/494; 252/363.5; 424/465; 427/2.15
[58] Field of Search ..................... 252/363.5; 424/465, 424/481, 482, 494; 427/2.15

[56] References Cited

U.S. PATENT DOCUMENTS

| | | | |
|---|---|---|---|
| 3,758,679 | 9/1973 | Seidler | 424/499 |
| 3,962,419 | 6/1976 | Mayama et al. | 424/482 X |
| 4,036,948 | 7/1977 | Kitamori et al. | 424/492 |
| 4,079,125 | 3/1978 | Sipos | 424/482 X |
| 4,177,254 | 12/1979 | Khan et al. | 427/2.15 X |
| 4,748,023 | 5/1988 | Tamás et al. | 424/494 X |
| 4,844,907 | 7/1989 | Elger et al. | 424/465 |
| 4,911,921 | 3/1990 | Denton et al. | 514/570 |
| 4,950,484 | 8/1990 | Olthoff et al. | 424/465 X |
| 5,288,501 | 2/1994 | Nürnberg et al. | 424/465 |
| 5,681,588 | 10/1997 | Kolter et al. | 424/464 |

FOREIGN PATENT DOCUMENTS

| | | |
|---|---|---|
| 0200252 | 12/1986 | European Pat. Off. . |
| 281200A | 9/1988 | European Pat. Off. . |
| 330284A | 8/1989 | European Pat. Off. . |
| 2259646 | 6/1974 | Germany . |
| 1560475 | 2/1980 | United Kingdom . |
| WO 92/19227 | 11/1992 | WIPO . |

OTHER PUBLICATIONS

O'Connor et al., (1985), *Drug Dev. Ind. Pharm. Sci.*, vol. 11, No. 9–10, pp. 1837–1857.
Elbers et al., (1992), *Drug Dev. Ind. Phar.*, vol. 18, No. 5, pp. 501–517.
Barato et al., (1984), *Labo–Pharma–Probl. Tech.*, vol. 352, pp. 401.
Scand. J. Gastroentererol, (1996), vol. 31, No. 1, pp. 49–53.
Jalal et al., *J. Pharm. Sci.*, (1972), vol. 61, No. 9, pp. 1446–1467.
Chalmers et al., (1976), *J. Pharm. Pharmac.*, vol. 28, pp. 234–238.

*Primary Examiner*—Richard D. Lovering
*Attorney, Agent, or Firm*—McDonnell Boehnen Hulbert & Berghoff

[57] ABSTRACT

A granulate, containing a drug having a solubility in water of 1:>10 and ≦15 weight percent of a water dispersible hydrocolloid incorporated into a fast-disintegrating and fast-dissolving composition.

7 Claims, No Drawings

GRANULATE FOR THE PREPARATION OF FAST-DISINTEGRATING AND FAST-DISSOLVING COMPOSITIONS CONTAINING A HIGH AMOUNT OF DRUG

The present invention relates to a granulate, containing a high amount of an active ingredient, and fast-disintegrating and dissolving compositions, containing the said granulate.

BACKGROUND OF THE INVENTION

It is well-known that for an effective treatment of diseases high doses of drugs and especially of antimicrobial compounds may have to be administered. In addition thereto there is a need to reduce the dosing frequency from 4 or 3 times daily to twice or once daily in order to increase patient compliance. The daily dose of a drug may thus be divided over 1 or 2 instead of 3 or 4 doses, which means that the amount of drug per dosage-form has to be increased. Some drugs, depending on their potency and pharmacokinetic properties can be suitably incorporated in so-called modified-release preparations. Other drugs, such as e.g. amoxicillin, appear to provide the best bioavailability when incorporated in dosage-forms having an immediate release of the active ingredient only (Scand. J. Gastroentererol. (1996) 31(1), pages 49–53). Since it is not convenient for a patient to take at the same time two or more small preparations containing the same medicament instead of one large preparation, especially not for the elderly who normally have to take multiple medications, there always has been a need for such easily swallowable dosage-forms, containing a maximum amount of drug and a minimum amount of excipients. Numerous attempts to realise such dosage-forms have been undertaken since the seventies.

I. M. Jalal et al. in J. Pharm Sci (1972) 61:9, pages 1466–1467, disclose tablets, containing 80% of a drug which is magnesium hydroxide, sulphadiazine or acetaminophen, and 20% of a binder which is Avicel® RC581 (microcrystalline cellulose and sodium carboxymethyl cellulose). Tablets were prepared by mixing the drug and the microcrystalline cellulose, granulating the blend with water, drying the granules and compressing these into tablets. Disintegration times varied from 0.8 minutes (magnesium hydroxide) to 3.5 minutes (sulphadiazine). In the present inventors' experience it has become clear that the results greatly depend on the properties of the drug: e.g. when they applied the above method to prepare tablets containing 80 wt % of amoxicillin trihydrate, a disintegration time of 12½ minutes was observed, tablets containing ibuprofen disintegrated after more than 5 minutes and tablets containing sulphamethoxazole required 35 minutes to disintegrate in water. The results, as obtained by Jalal for sulphadiazine and acetaminophen, could be rather well reproduced by the present inventors.

A. A. Chalmers et al. in J. Pharm. Pharmac. (1976) 28 pages 234–238, disclose tablet formulations containing a high amount (>90%) of oxytetracycline and optionally intragranular microcrystalline cellulose (7.2%) and/or alginic acid (2.7%). The tablets were prepared either by slugging or by the conventional wet granulation technique, using water or a 2.5 wt % solution of polyvinylpyrrolidone in water. Very fast disintegration times could be reached by tablets prepared by the slugging method only, provided also that alginic acid was incorporated in the granulate. When these techniques were applied to e.g. amoxicillin, also an antibiotic compound, no fast-disintegrating tablets could be obtained.

U.S. Pat. No. 1,560,475 discloses tablets containing more than 90% by weight of an orally active cephalosporin and consequently less than 10 wt % of excipients (binder, disintegrant and lubricant). The tablet can be prepared by admixing the cephalosporin and excipients and then compressing the mixture, but preferably the tablets are prepared by dissolving or dispersing the binder in water or a suitable organic solvent and using this liquid to granulate the cephalosporin. The dried granules are then mixed with the disintegrant and the lubricant and compressed into tablets. However, the disintegration time of such tablets as measured in distilled water at 37° C. ranges from 2 minutes to 13 minutes.

DE-2259646 discloses tablets containing about 90% of a cephalosporin compound and about 10% of excipients (crystalline cellulose, ultraamylopectin and a lubricant). The tablets are prepared by mixing the above ingredients, making a dry granulate and compressing the granules so obtained into tablets. The tablets disintegrate in artificial gastric juice at 37° C. within 3 minutes.

EP-0200252 discloses tablets containing 80–98% of a mixture, consisting of trimethoprim or a salt thereof and a sulfonamide or a salt thereof in a ratio between 1:20 and 20:1, and an ion-exchange compound of the artificial resin type, such as Amberlite® IRP 88. The tablets are prepared by a wet granulation technique using a solution containing a wet granulation binding agent in ethanol or a mixture of ethanol and water. Disintegration times were reported to be less than 1 minute in general, but the teachings of this application appeared to be not applicable to other drugs or combinations of drugs.

A formulation technique which is generally applicable to different drugs, having a solubility in water of less than 10% is disclosed in EP-0330284-B. The drug is blended with 20–100 wt % of a cellulose product, which is microcrystalline cellulose, microfine cellulose or a mixture thereof, and granulated with an aqueous solution, containing up to 0.5 wt % of a wet granulation binding agent, all percentages based on the weight of the active ingredient. After drying and sieving the granules they may be blended with suitable excipients, such as disintegrants, lubricants and flavours, to obtain fast-disintegrating tablets. A specific example thereof is disclosed in EP-0281200-B, which describes fast-disintegrating tablets, containing an amphoteric beta-lactam antibiotic, 24–70 wt % of a first disintegrant, which may be microcrystalline cellulose, and a second disintegrant. Disintegration times are reported to be within one minute in general. The bioavailability of e.g. amoxicillin trihydrate showed to be as good as that of a commercially available suspension and was independent of the way of administering the tablet (as a suspension after having allowed the tablet to disintegrate in water or as a swallowable tablet). However, this formulation technique appeared to be not applicable for the preparation of fast-disintegrating and fast-dissolving tablets, containing a higher amount of active ingredient and a considerably reduced amount of the cellulose product.

The problem to be solved by the present invention was to provide a formulation or manufacturing method, which would be generally applicable to all kinds of active ingredients having a solubility in water of less than 10%, for fast-disintegrating and fast-disssolving compositions, containing a high amount of such active ingredient, while using conventional production equipment.

SUMMARY OF THE INVENTION

The object of the present invention is to provide a granulate, containing a drug, having a solubility in water of 1:>10, and ≦15 wt %, most preferably 2–5 wt %, of a water dispersible hydrocolloid, the percentage based on the weight of the said drug.

The present invention also provides fast-disintegrating and fast-dissolving compositions, containing the said granulate in an amount of ≦80 wt % in admixture with suitable excipients, the percentage based on the weight of the composition, and optionally other compounds, selected from the group consisting of drugs and compounds enhancing the efficacy of the first drug (e.g. beta-lactamase inhibitors) in case the drug is a beta-lactam antibiotic.

DETAILED DESCRIPTION OF THE INVENTION

It has now been found that by making a blend of a drug, having a solubility in water of 1:>10, and ≦15 wt % of a water dispersible hydrocolloid, the percentage based on the weight of the drug, granulating the same with water and mixing the granules so obtained after drying with suitable excipients, such as disintegrants, lubricants, flavours and sweetening agents, in an amount as low as possible, fast-disintegrating and dissolving compositions can be prepared. More particularly such compositions, preferably containing a high amount of drug as well, comprise the above described granulate in an amount of at least 80 wt % in admixture with 2–8 wt % of a first disintegrant and 2–8 wt % of a second disintegrant, the percentages based on the weight of the composition. Optionally the compositions may also contain flavours, sweetening agents, such as saccharinic acid, the sodium salt thereof or aspartame, lubricants, such as colloidal silicon dioxide, stearic acid or a salt thereof, etc.

The water dispersible hydrocolloid to be used may be from an inorganic source, such as expanding lattice clays, like bentonite or montmorillonite. It can also be an organic substance such as a water dispersible cellulose, also known as microcrystalline cellulose and carboxymethyl cellulose sodium in the U.S. Pharmacopoeia/National Formulary. Four types of water dispersible celluloses, which are colloidal forms of microcrystalline cellulose, prepared by chemical depolymerisation of highly purified wood pulp, the original crystalline areas of the fibres being combined with sodium carboxymethyl cellulose and spray-dried, have been marketed under the trade names Avicel® RC-501 (containing 7.1–11.9% of sodium carboxylmethyl cellulose), Avicel® RC-581 (containing 8.3–13.8% of sodium carboxymethyl cellulose), Avicel® RC-591 (containing 8.3–13.8% of sodium carboxymethyl cellulose) and Avicel® CL-611 (containing 11.3–18.8% of sodium carboxymethyl cellulose). All types are hygroscopic powders, which are insoluble in organic solvents and dilute acids, and partially soluble in both dilute alkali and water (due to the sodium carboxymethyl cellulose component). Although all four types may be used to prepare the granulate according to the invention, preferably the Avicel® RC 581 type is used, but most advantageously the Avicel® RC 591 type is incorporated in the granulate in an amount of ≦15 wt %. Preferably the hydrocolloid is used in a concentration of between 1 and 10 wt %, but more advantageously in a concentration ranging from 2 to 5 wt %, all percentages based on the weight of the drug.

The drugs, to be incorporated in the granulate have a solubility in water of 1:>10 at room temperature, but preferably the solubility is 1:≧100. Advantageously those drugs are used which have to be administered in high doses to be effective. Examples of such drugs are antimicrobial compounds in general, selected from the group of beta-lactam compounds, such as the penicillins (amoxicillin trihydrate, ampicillin) and cephalosporins (cefaclor); the group of macrolides, such as erythromycin and josamycin; the group of sulphonamides, such as sulphamethoxazole; the group of hydroxyquinolones and quinolones, such as ciprofloxacin; the group of imidazoles and nitroimidazoles, such as metronidazole and iinidazole; and various other compounds, such as nalidixic acid, and nitrofirantoin. However other drugs, not belonging to the antimicrobial compounds, can also be successfully granulated according to the present invention: antacids, such as hydrotalcite, analgesic and anti-inflammatory drugs, such as. ibuprofen, acetaminophen and acetylsalicylic acid, antidiabetic agents, such as tolbutamide, antimalarials, such as amodiaquine hydrochloride, tuberculostatics and tuber-culocides, such as rifampicin, anticonvulsants, such as carbamazepine, and dopaminergic agents, such as levodopa.

The granulates according to the present invention are prepared according to methods as known in the art e.g. as taught by I. M. Jalal et al. Preferably the drug and water dispersible hydrocolloid are blended and water is added until the material is sufficiently wetted. The amount of water used may range from 20 to 30 wt %, based on the weight of the granulate. After partial drying the wet mass is passed through a first screen and subsequently further dried in a fluidized bed dryer at an air inlet temperature of between 40° and 60° C. After drying the granules are passed through a second screen. Alternatively the wet mass is transferred to a fluidized bed dryer without wet screening. After drying the granules are passed through a first and a second screen and optionally a third screen respectively.

Whereas many of the above-mentioned drugs have unsatisfactory flow-properties, the granulates according to the invention have sufficient to good flow properties. Due to a good bulk volume and a proper Hausner ratio they can be easily processed into compositions. Disintegration and dissolution behaviour of the granulates are also satisfactory.

The compositions, based on the above granulate, preferably contain the granulate in an amount of ≧80 wt % in order to comply with the requirement to provide a high-dosed composition. It goes without saying that the granulate can also be incorporated in a dosage-form together with a greater part of excipients.

In order to prepare fast-disintegrating and fast-dissolving compositions, containing a high amount of drug, the granulate is advantageously blended with a first disintegrant and a second disintegrant and optionally other excipients such as a lubricant, flavours, sweetening agents. The first disintegrant is preferably a cellulose product, which is microcrystalline cellulose (Avicel® PH 101, Avicel® PH 102), microfine cellulose or a mixture thereof. The second disintegrant is selected from the group of superdisintegrants, such as cross-linked polyvinylpyrrolidone and low-substituted hydroxypropyl cellulose. Both the first and the second disintegrant are advantageously added in an amount of 2–8 wt %, more preferably 3–6 wt %, the percentage based on the weight of the composition. Most preferably the ratio of the amount of the first and the second disintegrant in the composition is 1:1.

Optionally the granulate can be blended with a drug or a compound which enhances the activity of the drug incorporated in the granulate, such as a beta-lactamase inhibitor in case the drug is a beta-lactam compound.

By fast disintegration is meant a disintegration time in water of room temperature of less than 2 minutes and preferably less than one minute. Fast dissolution is to be considered as >95% of the drug dissolved in water of 37° C. after 30 minutes. Preferably 90% of the drug has been dissolved after 10 minutes (same conditions).

The compositions according to the present invention show many advantages. In a bioequivalence study an amoxicillin- and a cefaclor-containing tablet according to the present invention have proved to be equivalent to commercially available compositions. Furthermore, the variation in disintegration time and dissolution between compositions, containing a different medicament in a similar carrier, as shown by the prior art compositions described above, has been reduced. By using the high-dosed granulate a considerable reduction of the volume of the dosage-form has been achieved. The advantages thereof are not only apparent to the patient, who can easily swallow the new composition, as a consequence of which patient compliance will be increased. Due to the reduction of the amount of excipients to be used, the new compositions also have advantages from both an economical and an environmental point of view, such as a reduction of waste from aluminum and polyvinylchloride which packaging materials cannot be recycled.

Although the foregoing invention has been described in some detail by way of illustration and example for purposes of clarity and understanding, it will be readily apparent to those of ordinary skill in the art in the light of the teachings of this invention that certain changes and modifications may be made thereto without departing from the spirit and the scope of the appended claims.

The following examples further illustrate the invention.

EXAMPLES

Example 1

Fast-disintegrating tablet composition

| | |
|---|---|
| Amoxicillin (as trihydrate) | 86.9% |
| microcrystalline cellulose and sodium carboxymethyl cellulose (Avicel ® RC591) | 2.6% |
| cross-linked polyvinylpyrrolidone | 3.8% |
| microcrystalline cellulose | 3.8% |
| flavours | 1.6% |
| sweetening agent | 1.0% |
| lubricant | 0.4% |

The disintegration time in water of 20° C. was 48–50 seconds.

Dissolution: 98.5% of amoxicillin dissolved after 30 minutes

Mean tablet weight: 1330 mg

Hardness: 20 kP

Friability: <0.01%

Example 2

Preparation of a granulate 970 g of cefaclor (as monohydrate) and 30 g of microcrystalline cellulose and sodium carboxymethyl cellulose (Avicel® RC591) were mixed for 5 minutes in a planetary mixer. Gradually about 320 ml of water was added to this blend and mixing was continued for another 5 minutes. The wet granulate was dried in a fluidised bed dryer at an air inlet temperature of 50° C. and subsequently sieved through a 1.00 mm and 0.630 mm screen respectively.

Example 3

Preparation of fast-disintegrating tablets 864 g of the granulate obtained according to example 2 was mixed with 98 g of a mixture of microcrystalline cellulose and cross-linked polyvinylpyrrolidone (1:1), flavours and sweetening agents in a TURBULA-mixer for 10 minutes. After a lubricant was added mixing was continued for another 3 minutes and the mixture was compressed into tablets, having a mean weight of 625 mg.

Friability: <0.01%

Hardness: 6.9 kP

Mean tablet weight: 627 mg

Disintegration time: 22 sec.

Dissolution:

| % cefaclor dissolved: | after: |
|---|---|
| 98 | 10 min |
| 99 | 30 min |

Example 4

Fast-disintegrating tablet composition

| | |
|---|---|
| Cefaclor monohydrate | 524 mg |
| microcrystalline cellulose and sodium carboxymethyl cellulose (Avicel ® RC591) | 15.72 mg |
| microcrystalline cellulose | 13.5 mg |
| low-substituted hydroxypropyl cellulose | 13.5 mg |
| flavour | 9.1 mg |
| sweetening agent | 9.1 mg |
| lubricants | 9.2 mg |

Friability: <0.01%

Hardness: 7.4 kP

Mean tablet weight: 597 mg

Disintegration time: 100 sec.

Dissolution:

| % cefaclor dissolved: | after: |
|---|---|
| 92 | 10 min |
| 96 | 30 min |

Example 5

Fast-disintegrating tablet composition

| | |
|---|---|
| granulate (= amoxicillin (as trihydrate)/microcrystalline cellulose and sodium carboxymethyl cellulose (Avicel ® RC591) 95/5) | 84.1% |
| cross-linked polyvinyl pyrrolidone | 6.3% |
| microcrystalline cellulose | 6.3% |
| flavours | 1.6% |
| sweetening agent | 1.0% |
| lubricant | 0.7% |

| hardness (kP) | disintegration time (water 20° C.) (seconds) |
|---|---|
| 7 | 52–56 |
| 11 | 56–61 |
| 18 | 58–62 |

Example 6

| | |
|---|---|
| granulate | 89.6% |
| (= amoxicillin (as trihydrate)/microcrystalline cellulose and sodium carboxymethy cellulose (Avicel ® RC581) 98/2) | |
| cross-linked polyvinyl pyrrolidone | 3.9% |
| microcrystalline cellulose | 3.9% |
| flavours | 1.6% |
| sweetening agent | 1.0% |

The disintegrationtine in water of 20° C. was 92 seconds, The observed hardness of the tablet was 7 kP.

Example 7

| | |
|---|---|
| granulate | 84.75% |
| (= amoxicillin (as trihydrate)/microcrystalline cellulose and sodium carboxymethyl cellulose (Avicel ® RC581) 97/3) | |
| cross-linked polyvinyl pyrrolidone | 4% |
| microcrystalline cellulose | 11% |
| lubricant | 0.25% |

| hardness (kP) | disintegration time (seconds) |
|---|---|
| 6 | 102 |
| 12 | 120 |
| 18 | 114 |

Example 8

| | |
|---|---|
| granulate | 84% |
| (= amoxicillin (as trihydrate)/microcrystalline cellulose and sodium carboxymethyl cellulose (Avicel ® RC581) 96/4) | |
| cross-linked polyvinyl pyrrolidone | 4% |
| microcrystalline cellulose | 8.7% |
| lubricant | 3.3% |

| hardness (kP) | disintegration time (seconds) |
|---|---|
| 5 | 94 |
| 9 | 90 |
| 15 | 115 |

Example 9

| | |
|---|---|
| granulate | 89.35% |
| (= amoxicillin (as trihydrate)/microcrystalline cellulose and sodium carboxymethyl cellulose (Avicel ® RC581) 92/8) | |
| cross-linked polyvinyl pyrrolidone | 4% |
| microcrystalline cellulose | 6.4% |
| lubricant | 0.25% |

The disintegration time in water of 20° C. was 80 seconds. The observed hardness of the tablet was 6 kP.

We claim:

1. A granulate comprising a drug having a solubility in water of 1:>10 in admixture with a water dispersible cellulose, which is a microcrystalline cellulose and sodium carboxymethyl cellulose, wherein the water dispersible cellulose is present in an amount of ≦15 weight percent based on the weight of the drug.

2. The granulate according to claim 1, wherein the granulate contains between about 1 to about 10 weight percent of the water dispersible cellulose.

3. The granulate according to claim 1, wherein the granulate contains between about 2 to about 4 weight percent of the water dispersible cellulose.

4. The granulate according to claim 1, wherein the water dispersible cellulose contains 8.3–13.8 weight percent of sodium carboxymethyl cellulose.

5. The granulate according to claim 1, wherein the granulate is made by wet granulation and subsequent sieving of the granulate.

6. A fast-disintegrating and fast-dissolving composition comprising ≦80 weight percent of the granulate of claim 1 admixed with from about 2 to about 8 weight percent of a first disintegrant selected from the group consisting of microcrystalline cellulose, a microfine cellulose, and mixtures thereof and from about 2 to about 8 weight percent of a second disintegrant selected from the group consisting of cross-linked polyvinylpyrrolidone and low-substituted hydroxypropyl cellulose, all percentages based on the weight of the composition.

7. The composition according to claim 6, wherein the first disintegrant and the second disintegrant are present in a 1:1 ratio.

* * * * *